US00PP08225P

United States Patent [19]

VandenBerg

[11] Patent Number: Plant 8,225

[45] Date of Patent: May 11, 1993

[54] CHRYSANTHEMUM PLANT NAMED BRONZE MELOSA

[75] Inventor: Cornelis P. VandenBerg, Salinas, Calif.

[73] Assignee: Yoder Brothers, Inc., Barberton, Ohio

[21] Appl. No.: 715,632

[22] Filed: Jun. 14, 1991

[51] Int. Cl.[5] ..... A01H 5/00

[52] U.S. Cl. ..... Plt./79

[58] Field of Search ..... Plt./76, 79

[56] References Cited

U.S. PATENT DOCUMENTS 4,616,099 10/1986 Sparkes ..... 800/1

OTHER PUBLICATIONS

Gosling, ed. 1979. "The Chrysanthemum Manual-6th edition" The National Chrysanthemum Society, London, Esses Telegraph Press, Ltd., pp. 329-336.

Broertjes et al. 1978. "Application of mutation breeding methods in the improvement of vegetatively propagated crops", Elsevier Sci. Pub. Co., New York, pp. 162-175.

Broertjes et al. 1980. "A mutant of a mutant of a mutant of a . . . Irradiation of progressive radiation-induced mutants in a mutation breeding programme with *Chrysanthemum morifolium*", Euphtica, 29: 526-530.

Searle, et al. 1968. "Chrysanthemums the Year Round", Blanford Press, London, pp. 27-29, 320-327.

Chan. 1966. "Chrysanthemum and rose mutations induced by X-rays", Am. Soc. Hart. Sci. Proc., pp. 613-620.

Broertjes, 1966. "Mutation breeding of Chrysanthemums", Euphytica, 15:156-162.

Dowrick et al. 1966. "The induction of mutations in Chrysanthemum using X- and gamma radiation", Euphytica, 15:204-210.

*Primary Examiner*—Howard J. Locker

*Attorney, Agent, or Firm*—Foley & Lardner

[57] ABSTRACT

A Chrysanthemum plant named Bronze Melosa particularly characterized by its flat capitulum form; decorative capitulum type; light-orange ray floret color with slightly darker center; diameter across face of capitulum of 89 to 102 mm when fully opened, when grown as a single stem spray cut mum; photoperiodic flowering response to short days in Salinas under normal temperatures is 47 to 57 days after start of short days; flowering response in Bogota, Colombia, under temperatures of minimum 6.3 degrees Celsius night and maximum 29 degrees Celsius day is 65 to 72 days; plant height, with 6 to 8 long days prior to start of short days ranges from 79 to 91 cm when grown in Salinas as a single stem cut mum with no growth regulator applications; when grown in Bogota, with 14 to 15 long days prior to start of short days, plant height ranges from 99 to 124 cm; peduncle length of the first lateral at flowering after removing the apical bud ranges from 10 to 15 cm when grown in Salinas, and from 13 to 18 cm when grown in Bogota; peduncle length of the fourth lateral ranges from 18 to 20 cm in Salinas, and from 20 to 23 cm in Bogota; and excellent tolerance to low night temperatures for bud initiation and flower development.

1 Drawing Sheet

The present invention comprises a new and distinct cultivar of Chrysanthemum, botanically known as *Dendranthema grandiflora*, and referred to by the cultivar name Bronze Melosa.

Bronze Melosa, identified as 3448 (85-268A08), is a product of a mutation induction program. The new cultivar was discovered and selected by Cornelis P. VandenBerg in November 1988 in a controlled environment in Salinas, Calif., as one flowering plant within a flowering block established as rooted cuttings from stock plants which has been exposed as unrooted cuttings to an X-ray source of 2000 rads in Ft. Meyers, Fla., in March 1988. The irradiated parent cultivar was the cultivar identified as Melosa, disclosed in U.S. Plant Pat. No. 7,465.

The irradiation program resulting in Bronze Melosa had as its primary objective the expansion of color ranges of the parent cultivar Melosa. The irradiation program comprised irradiating cuttings of the parent cultivar at irradiation levels of 1500, 1750 and 2000 rads. A total of 1,324 cuttings harvested from a total of 225 irradiated plants were planted on September 19, September 12 and September 5, respectively. A resupply of material irradiated at 1500 rads was planted on Oct. 3, 1988. Of the total cuttings planted, 20 initial selections were made, which selections were then revegetated and reflowered. Two consecutive flowerings resulted in discarding 6 of the original 20 selections on Jul. 25, 1989. Because of the potential importance of the parent cultivar Melosa, it was decided to flower all remaining 14 selections in Bogota, Colombia, and to re-flower the same selections in Salinas, as Active status plants. Flowering in Bogota resulted in discarding 12 of these 14 selections on Apr. 10, 1990, and the decision to introduce one selection (3448) as Bronze Melosa. During a flowering in Salinas, on Jun. 19, 1990, one remaining selection was discarded, and two selections, which were previously discarded in Bogota were re-instated as Dark Melosa (3456) and Coral Melosa (3458) for possible introduction in the United States only.

The first act of asexual reproduction of Bronze Melosa was accomplished when vegetative cuttings were taken from the initial selection in January 1989 in a controlled environment in Salinas, Calif., by technicians working under supervision of Cornelis P. VandenBerg.

Horticultural examination of controlled flowerings of successive plantings has shown that the unique combination of characteristics as herein disclosed for Bronze Melosa are firmly fixed and are retained through successive generations of asexual reproduction.

Bronze Melosa has not been observed under all possible environmental conditions. The phenotype may vary significantly with variations in environment such as temperature, light intensity and daylength.

The following observations, measurements and comparisons describe plants grown in Salinas, Calif., and in Bogota, Colombia, under greenhouse conditions which approximate those generally used in commerical greenhouse practice. The low night temperature tolerance was determined in repeated flowerings in Bogota, Colombia, with an average minimum low night temperature inside the greenhouse during our trials ranging from 6.3 to 10.0 degrees Celsius.

The following traits have been repeatedly observed and are determined to be basic characteristics of Bronze Melosa, which, in combination, distinguish this Chrysanthemum as a new and distinct cultivar:

1. Flat capitulum form.
2. Decorative capitulum type.
3. Light-orange ray floret color with slightly darker center.
4. Diameter across face of capitulum of 89 to 102 mm when fully opened, when grown as a single stem spray cut mum.
5. Photoperiodic flowering response to short days in Salinas under normal temperatures is 47 to 57 days after start of short days. Flowering response in Bogota, Colombia under temperatures of minimum 6.3 degrees Celsius night and maximum 29 degrees Celsius day is 65 to 72 days.
6. Plant height, with 6 to 8 long days prior to start of short days, ranges from 79 to 91 cm when grown in Salinas as a single stem cut mum with no growth regulator applications, when grown in Bogota, with 14 to 15 long days prior to start of short days, plant height ranges from 99 to 124 cm.
7. Penduncle length of the first lateral at flowering after removing the apical bud ranges from 10 to 15 cm when grown in Salinas, and from 13 to 18 cm when grown in Bogota. Peduncle length of the fourth lateral ranges from 18 to 20 cm in Salinas, and from 20 to 23 cm in Bogota.
8. Excellent tolerance to low night temperatures for bud initiation and flower development.

The accompanying photographic drawing is a view of a single stem of Bronze Melosa, with the colors being as nearly true as possible with illustrations of this type.

Of the commercial cultivars known to the inventor, the most similar in comparison to Bronze Melosa is the parent cultivar Melosa. All traits of Bronze Melosa are similar to those of Melosa, except for the ray floret color. The ray floret color of Bronze Melosa is light orange, while the ray floret color of Melosa is described as soft lavener-pink.

In the following description color references are made to The Royal Horticultural Society Colour Chart. The color values were determined on plant material grown as a single stem spray cut mum in Salinas, Calif., on Jun. 29, 1990.

Classification:

*Botanical.*—*Dendranthema grandiflora* cv Bronze Melosa.

*Commercial.*—Flat decorative spray cut mum.

Inflorescence

A. Capitulum:

*Form.*—Flat.

*Type.*—Decorative.

*Diameter across face.*—89 to 102 mm when fully opened.

B. Corolla of ray florets:

*Color (general tonality from a distance of three meters).*—Light orange.

*Color (upper surface).*—Closest to 16A to 24B, slightly overlaid wtih 168C. Center of flower and immature buds are more strongly overlaid wtih 168C.

*Color (under surface).*—Closest to 16A to 16B.

*Shape.*—Slight longitudinal reflexing. Cross-section slightly concave.

C. Corolla of disc florets:

*Color (mature).*—14A.

*Color (immature).*—144B.

D. Reproductive organs:

*Androecium.*—Present on disc florets only; very few disc florets, barely visible in the mature flower, scant pollen.

*Gynoceium.*—Present on both ray and disc florets.

PLANT

A. General appearance:

*Height.*—79 to 91 cm when grown in Salinas as a single stem cut mum with 6 to 8 long days after planting rooted cutting prior to start of short days, with no growth regulator applications; when grown in Bogota, with 14 to 15 long days prior to start of short days, plant height ranges from 99 to 124 cm.

B. Foliage:

*Color (upper surface).*—147A.

*Color (under surface).*—147B.

*Shape.*—Deeply lobed and slightly serrated.

I claim:

1. A new and distinct Chrysanthemum plant named Bronze Melosa, as described and illustrated.

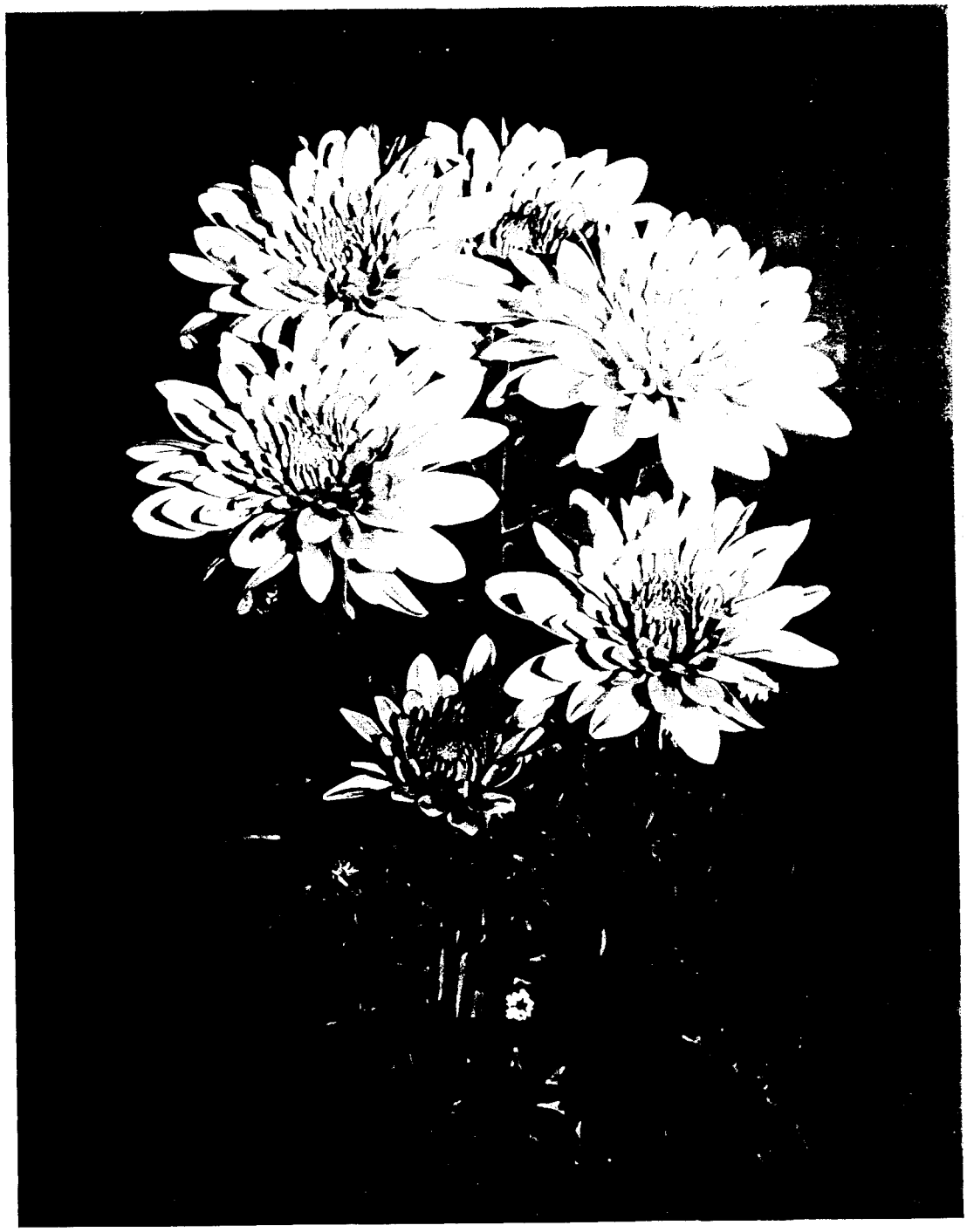

* * * * *